United States Patent [19]
Chaplan et al.

[11] Patent Number: 5,849,737
[45] Date of Patent: Dec. 15, 1998

[54] COMPOSITIONS AND METHODS FOR TREATING PAIN

[75] Inventors: Sandra Reading Chaplan, San Diego, Calif.; Flemming Winther Bach, Aarhus, Denmark; Tony Lee Yaksh, San Diego, Calif.

[73] Assignee: The Regents of the University of California, Oakland, Calif.

[21] Appl. No.: 422,377

[22] Filed: Apr. 14, 1995

[51] Int. Cl.$^6$ .......................... A61K 31/535; A61K 31/16
[52] U.S. Cl. ...................... 514/238.8; 514/626; 514/567; 514/315; 514/255; 514/237.8
[58] Field of Search .................................... 514/626, 567, 514/315, 255, 237.8, 238.8

[56] References Cited

U.S. PATENT DOCUMENTS 5,389,630   2/1995   Sah et al. ................................ 514/218

OTHER PUBLICATIONS

TOXLIT abstract AN 90:30068, Oda et al, "Metabolism of lidocaine by purified rat liver microsomal cytochrome P–450 isozymes", Biochem Paharmacol, vol. 38, No. 24., pp. 4439–4444, Jan. 1989.
Anesthesiology (1979) 51: 2; 123–126, Dohi S., et al., *An Analgesic Action of Intravenously Administered Lidocaine on Dorsal–Horn neurons Responding to Noxious Thermal Stimulation*.
Anesthesiology (1992) 76;513–517, Chabal C., et al., *The Use of Oral Mexiletine for the Treatment of Pain after peripheral Nerve Injury*.
Anesthesiology (1994) 80:2; 383–391, Abram S.E., et al., *Systemic Lidocaine Blocks Nerve Injury–Induced Hyperalgesia and Nociceptor–Driven Spinal Sensitization in the Rat*.
Brain Res. (19192) 603:2201–206, Biella G., et al., *Central Effects of Systemic Lidocaine Mediated by Glycine Spinal Receptors: An Iontophoretic Study in the Rat Spinal Cord*.
Br. Med. J. (1986) 292:173, Kastrup J., et al., *Treatment of Chronic Painful Diabetic Neuropathy with Intravenous Lidocaine Infusion*.
Can. Med. Assoc. J. (1943)49:478–481, Gordon R.A., *Intravenous Novocaine for Analgesia in Burns*.
Clin. J. Pain (1989)5:3239–244, Kastrup J., et al., *Lidocaine Treatment of Painful Diabetic Neuropathy and Endogenous Opioid Peptides in Plasma*.
Clin. Pharm. Ther. (1978) 24:654–662, Narang P.K., et al., *Lidocaine and Its Active Metabolites*.
JAMA (1961) 176:1041–1043, Shanbrom E., *Treatment of Herpetic Pain and Postherpetic Neuralgia with Intravenous Procaine*.
Pharmacol. Exp. Ther. (1972) 180:454–463, Keenaghan J.B., et al., *The Tissue Distribution, Metabolism and Excretion of Lidocain in Rats, Guinea Pigs, Dogs and Man*.
Journal of the American Academy of Dermatology (1986) 15:2:383–385, Juhlin L., *Long–standing Pain Relief of Adiposis Dolorosa(Dercum's Disease) after Intravenous Infusion of Lidocaine*.

Lancet (1988) 1:8575–6:9–11, Dejgård A., et al., *Mexilitine for Treatment of Chronic Painful Diabetic Neuropathy*.
Neurology (1991) 41:7; 1024–1028, Rowbotham M.C., et al., *Both Intravenous Lidocaine and Morphine Reduce the Pain of Postherpetic Neuralgia*.
Pain(1985)23:361–374, Woolf C.J., et al., *The Systemic Administration of Local Anesthetics Produces a Selective Depressions of C–afferent Fibre Evoked Activity in the Spinal Cord*.

(List continued on next page.)

Primary Examiner—Keith D. MacMillan
Attorney, Agent, or Firm—Fulbright & Jaworski

[57] ABSTRACT

Compositions and methods for alleviating pain (in particular, neuropathic pain) in a mammalian patient, wherein an effective amount of a physiologically-acceptable salt of a compound of the general formula

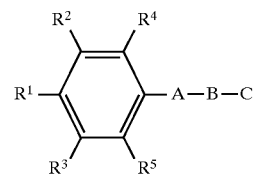

wherein each of $R^1$, $R^2$ and $R^3$ is independently selected from the group consisting of hydrogen, hydroxyl, acyl, alkoxyl, alkyl, aryl, alkylaryl, arylalkyl, hydroxyalkyl, hydroxyaryl, alkoxyalkyl, alkoxyaryl and $NR^8R^9$, in which each of $R^8$ and $R^9$ is independently selected from the group consisting of hydrogen, alkyl, aryl, acyl, alkylaryl, arylalkyl, hydroxyalkyl, hydroxyaryl, alkoxyalkyl and alkoxyaryl, with the proviso that at least one of $R^1$, $R^2$ and $R^3$ is hydroxyl;

each of $R^4$ and $R^5$ is independently selected from the group consisting of hydrogen, halogen and lower alkyl;

A is —C(=O)O— or $NR^{10}C(=O)$—, in which $R^{10}$ is selected from the group consisting of hydrogen, alkyl, aryl, alkylaryl, arylalkyl, hydroxyalkyl, hydroxyaryl, alkoxyalkyl and alkoxyaryl;

B is $—(CR^{11}R^{12})_n—$, in which each of $R^{11}$ and $R^{12}$ is independently selected from the group consisting of hydrogen, halogen, hydroxyl, alkoxyl, alkyl, aryl, acyl, alkylaryl, arylalkyl, hydroxyalkyl, hydroxyaryl, alkoxyalkyl and alkoxyaryl, and n is an integer from 1 to 5; and C is $NR^6R^7$, in which each of $R^6$ and $R^7$ is independently selected from the group consisting of hydrogen, alkyl, aryl, acyl, alkylaryl, arylalkyl, hydroxyalkyl, hydroxyaryl, alkoxyalkyl and alkoxyaryl, or $R^6$ and $R^7$ together form a heterocycle or substituted heterocycle selected from the group consisting of piperidyl, N-alkylpiperidyl, piperazinyl, N'-alkylpiperazinyl, morpholinyl and N-alkylmorpholinyl, is administered in a pharmaceutically acceptable carrier or excipient.

22 Claims, 7 Drawing Sheets

OTHER PUBLICATIONS

Pain(1987)28:69–75, Kastrup J., et al., *Intravenous Lidocaine Infusion—A New Treatment of Chronic Painful Diabetic Neuropathy?*.

Pain(1987)28:45–50, Lindström P., et al., *The Analgesic Effect of Tocainide in Trigeminal Neuralgia*.

Pain(1987)28:1;77–80, Peterson P., et al., *Dercum's Disease (Adiposis Dolorosa). Treatment of the Severe Pain with Intravenous Lidocaine*.

Pain(1989)38:333–338, Chabal C., et al., *The effect of Intravenous Lidocaine, Tocainide, and Mexiletine on Spontaneously Active Fibers Originating in Rat Sciatic Neuromas*.

Pain(1990)40:129–34, Bach F.W., et al., *The Effect of Intravenous Lidocaine on Nociceptive Processing in Diabetic Neuropathy*.

Pain(1991)45:2; 145–148 Brose, W.G., et al., *Subcutaneous Lidocaine for Treatment of Neuropathic Cancer Pain*.

Pain(1992)48:2;261–268, Devor M., et al., *Systemic Lidocaine Silences Ectopic Neuroma and DRG Discharge without Blocking Nerve Conduction*.

Pain(1992)50:3; 355–363, Kim S.H., et al., *An Experimental Model for Peripheral Neuropathy Produced by Segmental Spinal Nerve Ligation in the Rat*.

Pain(1992)48:377–382, Marchettini P., et al., *Lidocaine Test in Neuralgia*.

Reg. Anesth.(1985)10:1–6, Edwards W.T., et al., *Intravenous Lidocaine in the Management of Various Chronic Pain States; a Review of 211 Cases*.

Somatosensory and Motor Research (1992)9;3; 227–233, Sotgiu M.L. et al., *Effect of Systemic Lidocain on Dorsal horn neuron Hyperactivity Following Chronic Peripheral Nerve Injury in Rats*.

The Medical Journal of Australia (1960); 27–28, Collins E.B., *The Use of Intravenous Procaine Infusion in the Treatment of Postherpetic Neuralgia*.

Chemical Abstracts AN 1989:212291, Hisamichi et al., 1987.

Chemical Abstracts AN 1980:22210, Minasyan et al, 1979.

COMPOSITIONS AND METHODS FOR TREATING PAIN

This invention was made with Government support under Grant No. DA-02110 and Training Grant No. T32NS07329, awarded by the National Institutes of Health. The Government has certain rights in this invention.

BACKGROUND OF THE INVENTION

The present invention relates generally to the fields of biology and medicine. In particular, the present invention is directed to compositions and methods for use in treatment for patients with pain, particularly as originating from chronic afferent input and/or injury to nervous tissue.

Following injury to a peripheral nerve, substantial functional alterations occur in both the peripheral and central nervous systems. Sustained, low-level ectopic spontaneous activity originates at the site of neuroma formation in large peripheral axons [Chabal C et al., Pain 38:333–338 (1989)] as well as in dorsal root ganglion cells [Kajander K C et al., Neurosci Lett 138:225–228 (1992)]. While the basis of this spontaneous electrical activity is not known, abnormalities of axonal sodium channel distribution have been described in association with demyelination after peripheral nerve injury [Devor M et al., J Neurosci 13:1976–1992 (1993); Devor M et al., Neurosci Lett 102:149–154 (1989)] that may lead to spontaneous fiber activity [Matzner O et al., Brain Res 597:92–98 (1992)]. In addition, the appearance after nerve injury of an unusual type of "modified rapidly adapting" cutaneous mechanoreceptor has been identified, which although not spontaneously active, shows abnormally prolonged, weak, irregular discharges to light mechanical stimuli [Na H S et al., J Neurophysiol 70:522–528 (1993)]. Prominent increases are also seen in the evoked activity of dorsal horn neurons which project supraspinally [Lombard M C et al., Pain 37:335–345 (1989); Palecek J et al., J Neurophysiol 68:1951–1966 (1992)]. Similar sustained central activity is demonstrable after the application of N-methyl-D-aspartate type glutamate agonists [Dickenson A H et al., Brain Res 424:402–406 (1987)] which leads not only to electrophysiological facilitation of neuronal responses but also to the behavioral manifestation of tactile allodynia [Bach F W et al., Ann Neurol 36:288A (1994)]. Thus, continued afferent pathway activity is linked to behavioral states wherein modest stimuli may evoke pronounced responses. These changes in electrical activity are associated with peripheral and central changes including alterations in receptor expression [Sato J et al., Science 251:1608–1610 (1991); Xie Y-K et al., Series B, Chemistry, Life Sciences and Earth Sciences 36:68–74 (1993)], second messenger function [Mao J et al., J Neurophysiol 70:470–481 (1993); Mao J R et al., Brain Res 588:144–149 (1992)], neurotransmitter production [Bennett G J et al., Neurochemical and anatomical changes in the dorsal horn of rats with an experimental painful peripheral neuropathy, Processing of Sensory Information in the Superficial Dorsal Horn of Spinal Cord, Edited by Cervero F, Bennett G J, Headley P, New York, Plenum pp 463–471 (1989)], likely neuronal dropout [Sugimoto T et al., Pain 42:205–213 (1990)], and possibly altered balance of inhibitory/excitatory neurotransmitters [Yaksh T, Pain 37:111–123 (1989)]. The sum total of these mechanisms may provide a scenario whereby nerve injury leads to an anomalous pain state.

A number of carefully executed clinical studies have shown that systemically administered local anesthetics may have analgesic properties that are specific to pain states resulting from damage to nerve tissue [Chabal C et al., Anesthesiology 76:513–517 (1992); Chabal et al. (1989), supra; Dejgard A et al., Lancet 1:9–11 (1988); Kastrup J et al., Br Med J 292:173 (1986); Kastrup J et al., Pain 28:69–75 (1987); Marchettini P et al., Pain 48:377–382 (1992); Rowbotham M C et al., Neurology 41:1024–1028 (1991)]. Analgesia in such neuropathic pain states is attained in the absence of motor or sensory conduction blockade, and at doses without toxic effects. Since neuropathic pain is otherwise difficult to treat and typically refractory to conventional analgesic agents, these studies have generated considerable interest.

Patients with painful diabetic neuropathy have been shown to benefit with reduced pain scores for several days from the intravenous administration of lidocaine, without alteration in thermal thresholds [Bach F W et al., Pain 40:29–34 (1990); Kastrup et al. 1986), supra]. Patients with pain due to peripheral nerve injury likewise reported decreases in spontaneous pain, albeit of short duration, after intravenous lidocaine [Marchettini et al. (1992), supra]. Orally administered available congeners of lidocaine also may be effective, as demonstrated by the analgesic effects of mexiletine in painful diabetic neuropathy [Dejgard et al. (1988), supra] and peripheral nerve injury [Chabal et al. (1992), supra], and tocainide in trigeminal neuralgia [Lindström P et al., Pain 28:45–50 (1987)].

Following peripheral nerve injury, humans may report both thermal hyperalgesia and tactile allodynia (i.e., pain evoked by light touch or brushing of the skin). Importantly, human psychophysical studies have documented that the predominant evoked pain complaint in peripheral nerve injury sufferers is allodynia [Bowsher D, Sensory change in postherpetic neuralgia, Herpes Zoster and Postherpetic Neuralgia, Edited by Watson CPN, Amsterdam, Elsevier Science Publishers B.V., pp 97–107 (1993); Wahren L K et al., Pain 48:237–244 (1992)].

Due to its well known properties of conduction blockade, lidocaine has been assayed in afferent systems primarily using electrophysiological assessments. A number of investigations have examined the effects of lidocaine on evoked or spontaneous neural activity. A systematic examination in patients with painful diabetic neuropathy [Bach et al. (1990), supra] has suggested a spinal or supraspinal effect site due to suppression of the centrally organized nociceptive flexion response. In addition, considerable evidence from the preclinical literature supports a spinal cord or supraspinal site of action of intravenously administered lidocaine in facilitated pain states [Dohi S et al., Anesthesiology 51:123–126 (1979); Sotgiu M L et al., NeuroReport 5:873- (1994); Sotgiu M L et al., Neuroreport 2:425–428 (1991); Sotgiu M L et al., Somatosensory and Motor Research 9:227–233 (1992); Woolf C J et al., Pain 23:361–374 (1985)]. Lidocaine, with an octanol: water distribution coefficient of 110 at 36° C., pH 7.4 [Strichartz G R et al., Anesth Analg 71:158–70 (1990)], distributes promptly to central nervous system structures after systemic administration [Usubiaga J E et al., Br J Anaesth 39:943–947 (1967)]. The effects of a systemically delivered dose appear more potent in central than in peripheral nervous structures. Although peripheral terminals clearly respond to lidocaine, they appear to do so only at a relatively high concentration.

A single study has derived in vitro dose-response curves for the suppressant effect of lidocaine on spontaneous activity in acutely injured peripheral terminals. The reported $ED_{50}$ of 5.7 μg/ml, however, reflects drug in an artificial, protein-free system [Tanelian D L et al., Anesthesiology 74:934–936 (1991)]; a substantially higher plasma concentration would in all likelihood be required for a comparable investigation in vivo, considering that lidocaine is extensively protein-bound in circulation. In whole animals, the $ED_{50}$ of intravenous lidocaine for discharge suppression in neuromata has been reported to be 6 mg/kg, whereas that for the dorsal root ganglion is lower, at 1 mg/kg [Devor M et al., Pain 48:261–268 (1992)], a dose which also yields suppression of polysynaptic (spinal cord) sural nerve evoked after discharges [Woolf et al. (1985), supra]. Dose-related suppression of neurons in Rexed lamina V to high threshold mechanical and noxious thermal stimuli is seen in decerebrate cats (plasma concentration=3–10 μg/ml) [Dohi et al. (1979), supra]. IV lidocaine (1–5 mg/kg) suppresses polysynaptic C-fiber evoked flexor responses to mustard oil and noxious heat, without evidence of conduction block at the peripheral terminal [Woolf et al. (1985), supra]. IV lidocaine (3–4 mg/kg) suppresses noxious-evoked activity in wide dynamic range neurons in the rat, and, in addition, selectively suppresses the increased wide dynamic range neuronal activity seen ipsilateral to chronic peripheral nerve injury [Sotgiu et. al. (1991), supra; Sotgiu et al. (1992), supra]. To date, no studies have specifically examined the effects of systemically administered lidocaine on supraspinal structures or descending pathways in the context of hyperalgesia or increased evoked responses.

Although much interest has been generated by the clinical use of orally available lidocaine congeners in neuropathic pain states, such as mexiletine (Mexitil®, Boehringer Ingelheim) [Chabal et al. (1992), supra] and tocainide (Tonocard®, Merck Sharp & Dohme) [Lindstrom et al. (1987), supra], such therapies are far from universally effective and in many cases are poorly tolerated due to side effects, including some which may be life-threatening. Determination of the structure-activity relationship is critical to discovery of the mechanism underlying relief.

It is an object of the present invention to provide compositions and methods which do not suffer from all of the drawbacks of the prior art methods.

SUMMARY OF THE INVENTION

In accordance with the present invention, there are provided compositions and methods for alleviating pain, and in particular neuropathic pain, in a mammalian patient, wherein an effective amount of a physiologically-acceptable salt of a compound of the general formula I

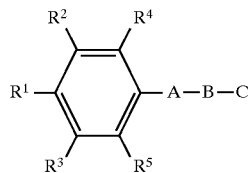

wherein each of $R^1$, $R^2$ and $R^3$ is independently selected from the group consisting of hydrogen, hydroxyl, acyl, alkoxyl, alkyl, aryl, alkylaryl, arylalkyl, hydroxyalkyl, hydroxyaryl, alkoxyalkyl, alkoxyaryl and $NR^8R^9$, in which each of $R^8$ and $R^9$ is independently selected from the group consisting of hydrogen, alkyl, aryl, acyl, alkylaryl, arylalkyl, hydroxyalkyl, hydroxyaryl, alkoxyalkyl and alkoxyaryl, with the proviso that at least one of $R^1$, $R^2$ and $R^3$ is hydroxyl;

each of $R^4$ and $R^5$ is independently selected from the group consisting of hydrogen, halogen and lower alkyl;

A is —C(=O)O— or $NR^{10}C$(=O)—, in which $R^{10}$ is selected from the group consisting of hydrogen, alkyl, aryl, alkylaryl, arylalkyl, hydroxyalkyl, hydroxyaryl, alkoxyalkyl and alkoxyaryl;

B is —$(CR^{11}R^{12})_n$—, in which each of $R^{11}$ and $R^{12}$ is independently selected from the group consisting of hydrogen, halogen, hydroxyl, alkoxyl, alkyl, aryl, acyl, alkylaryl, arylalkyl, hydroxyalkyl, hydroxyaryl, alkoxyalkyl and alkoxyaryl, and n is an integer from 1 to 5; and C is $NR^6R^7$, in which each of $R^6$ and $R^7$ is independently selected from the group consisting of hydrogen, alkyl, aryl, acyl, alkylaryl, arylalkyl, hydroxyalkyl, hydroxyaryl, alkoxyalkyl and alkoxyaryl, or $R^6$ and $R^7$ together form a heterocycle or substituted heterocycle selected from the group consisting of piperidyl, N-alkylpiperidyl, piperazinyl, N'-alkylpiperazinyl, morpholinyl and N-alkylmorpholinyl, is administered in a pharmaceutically acceptable carrier or excipient.

BRIEF DESCRIPTION OF THE DRAWINGS

The invention may be better understood with reference to the accompanying drawings, in which.

DETAILED DESCRIPTION OF THE INVENTION

Figure 1:
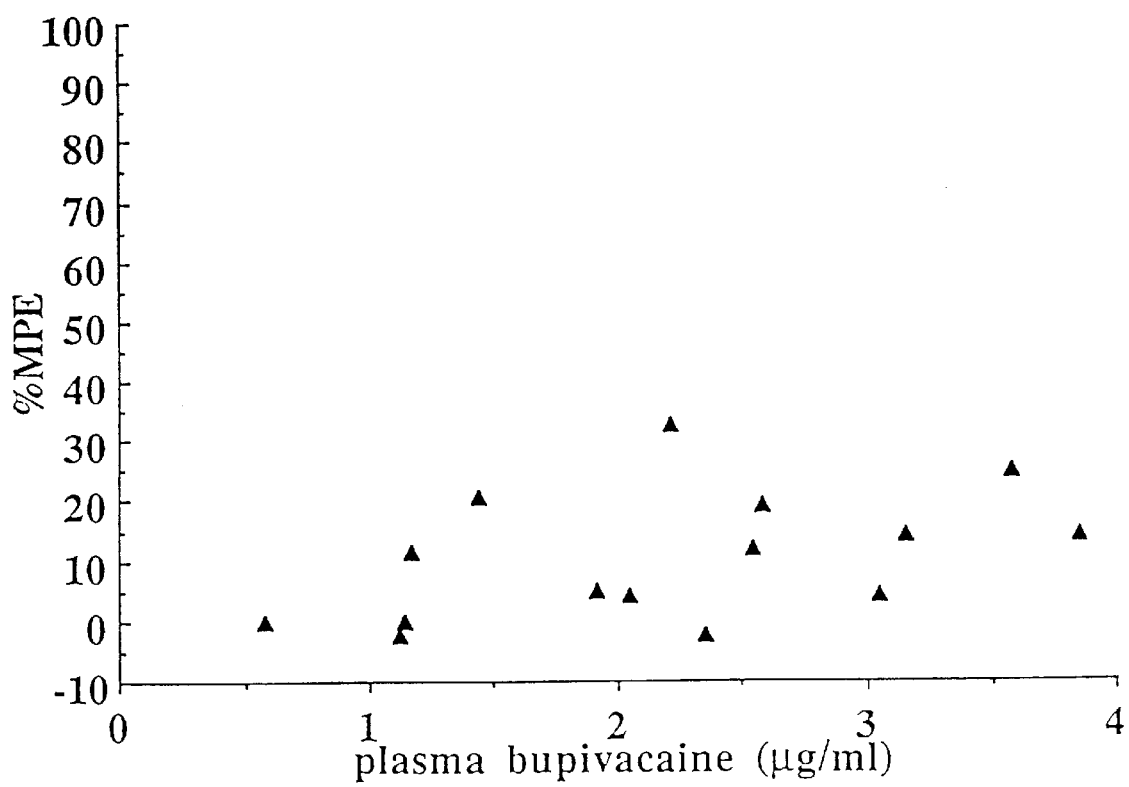
FIG. 1 illustrates the lack of correlation of plasma bupivacaine levels with percent of maximal possible drug effect on allodynia suppression (%MPE) illustrated up to plasma levels entering the toxic range (4 rats, 15 samples)

Pursuant to the present invention, compositions and methods for alleviating neuropathic pain in a mammalian patient are provided. These compositions and methods provide selective pain relief without loss of other sensory or motor modalities for a large class of patients, including those with pain related to cancer/treatments of cancer, AIDS, nerve injuries stemming from trauma, underlying diseases such as diabetes, infections such as herpes zoster, and degenerative disorders such as herniated discs. Moreover, the inventive compositions do not suffer from the drawbacks of previous treatment modalities, such as limited effectiveness and risk of serious side effects including the development of drug dependencies.

In the compositions and methods of the present invention, a physiologically acceptable salt of a compound of the general formula I

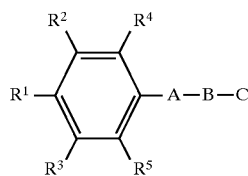

wherein each of $R^1$, $R^2$ and $R^3$ is independently selected from the group consisting of hydrogen, hydroxyl, acyl, alkoxyl, alkyl, aryl, alkylaryl, arylalkyl, hydroxyalkyl, hydroxyaryl, alkoxyalkyl, alkoxyaryl and $NR^8R^9$, in which each of $R^8$ and $R^9$ is independently selected from the group consisting of hydrogen, alkyl, aryl, acyl, alkylaryl, arylalkyl, hydroxyalkyl, hydroxyaryl, alkoxyalkyl and alkoxyaryl, with the proviso that at least one of $R^1$, $R^2$ and $R^3$ is hydroxyl;

each of $R^4$ and $R^5$ is independently selected from the group consisting of hydrogen, halogen and lower alkyl;

A is —C(=O)O— or $NR^{10}C(=O)$—, in which $R^{10}$ is selected from the group consisting of hydrogen, alkyl, aryl, alkylaryl, arylalkyl, hydroxyalkyl, hydroxyaryl, alkoxyalkyl and alkoxyaryl;

B is —$(CR^{11}R^{12})_n$—, in which each of $R^{11}$ and $R^{12}$ is independently selected from the group consisting of hydrogen, halogen, hydroxyl, alkoxyl, alkyl, aryl, acyl, alkylaryl, arylalkyl, hydroxyalkyl, hydroxyaryl, alkoxyalkyl and alkoxyaryl, and n is an integer from 1 to 5; and C is $NR^6R^7$, in which each of $R^6$ and $R^7$ is independently selected from the group consisting of hydrogen, alkyl, aryl, acyl, alkylaryl, arylalkyl, hydroxyalkyl, hydroxyaryl, alkoxyalkyl and alkoxyaryl, or $R^6$ and $R^7$ together form a heterocycle or substituted heterocycle selected from the group consisting of piperidyl, N-alkylpiperidyl, piperazinyl, N'-alkylpiperazinyl, morpholinyl and N-alkylmorpholinyl is employed. Preferred classes of compounds of general formula I include the 3-OH and 4-OH derivatives of the known compounds lidocaine, mepivacaine, bupivacaine, etidocaine and prilocaine:

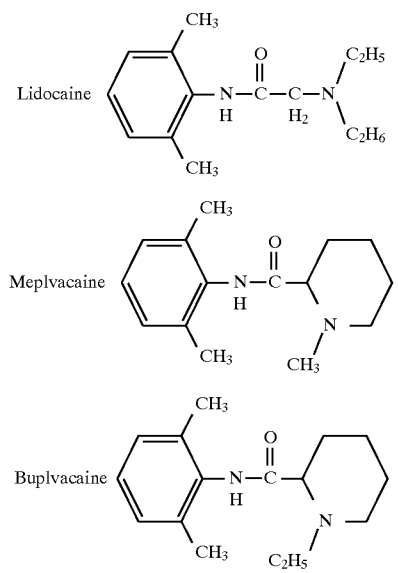

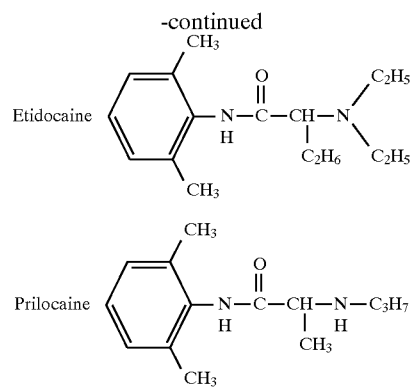

Pursuant to one particularly preferred embodiment, the active agent is a physiologically acceptable salt of 3-hydroxy-lidocaine [i.e., the compound of general formula I in which $R^1$ is H, $R^2$ is OH, $R^3$ is H, $R^4$ and $R^5$ are $CH_3$, A is —NHC(=O)—, B is —$CH_2$— and C is $N(CH_2CH_3)_2$]. Of the compounds of general formula I, apparently only the free base form of 3-OH lidocaine has been reported in the literature.

By "physiologically-acceptable salt" for purposes of the present invention is contemplated that the materials are capable of administration to or upon a mammal, including a human patient, without the production of undesirable physiological effects, including but not limited to neurotoxicity, nausea, dizziness, gastric upset and the like. Both unconjugated forms and free base forms solubilized by conjugation (for example, glucuronidated) are suitable for use in accordance with the present invention.

For purposes of the present invention, the terms "alkyl", "alkoxy" and "hydroxyalkyl" refer to groups comprising 1 to about 20 carbon atoms, preferably 1 to 5 carbon atoms. The term "acyl" refers to groups comprising 2 to about 20 carbon atoms, preferably 2 to 5 carbon atoms. The term "aryl" refers to aromatic ring systems comprising one to about three rings (e.g., phenyl, naphthyl, anthracyl, etc.).

As would be readily appreciated by those working in the field, the compounds of general formula I may be routinely synthesized using a variety of different approaches. For example, appropriate modifications of the heretofore-known methods for preparation of, e.g., the corresponding parent compounds that lack a 3-OH or 4-OH group may be employed. The synthesis of lead compound 3-hydroxy-lidocaine from lidocaine base has been reported [Keenaghan J B & Boyes R N, J. Pharmacol. Exper. Therapeut. 180:454–463 (1972)]; appropriate modification of this method (e.g., selection of corresponding starting materials to produce the desired product) is exemplary of available approaches to synthesis of a compound of general formula I with a 3-OH group.

Scheme 1 illustrates one synthetic approach for an exemplary 4-OH compound; similarly, Scheme 2 illustrates a synthetic approach for an exemplary 3-OH compound. For both types of compounds, of course, various alternatives are available and would be immediately apparent to those working in the field.

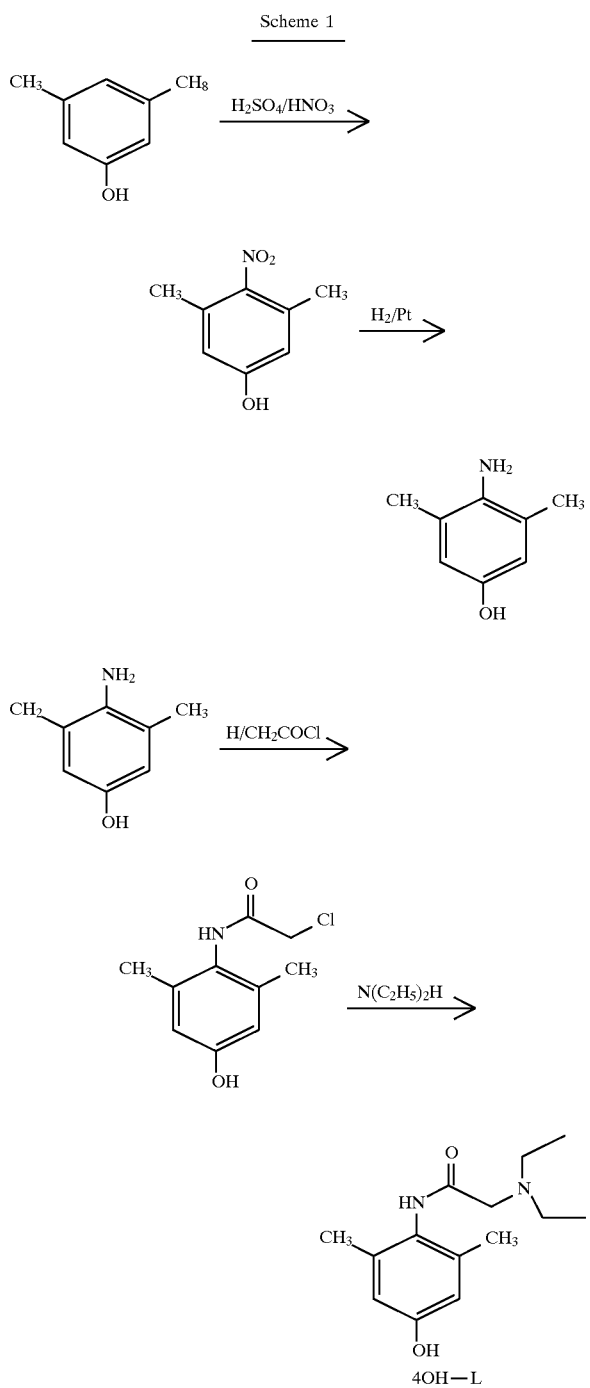

The free base forms of the compounds of general formula I are not water-soluble; for example, it was necessary to dissolve the free base of 3-hydroxylidocaine in a vehicle containing an empirically determined mixture of ethanol, dimethyl sulfoxide, propylene glycol and saline for application to the rat spinal cord. The physiologically-acceptable salt forms of the compounds of general formula I employed in accordance with the present invention, in contrast, are generally water-soluble to at least some degree, and the solubility properties thereof can be in many cases improved by conjugation. Unlike the free base forms of the compounds of general formula I, the salt forms may be administered by a variety of known routes [e.g., oral intravenous, intrathecal, local (e.g., intraneuromal), epidural, transdermal, etc.] as would be readily appreciated by those skilled in the art. As is conventional practice in the art, the active agent of general formula I is typically administered in a pharmaceutically acceptable carrier or excipient (e.g., saline).

The preparation of a pharmacological composition which contains active ingredients dissolved or dispersed therein is well understood in the art. Typically, such compositions are prepared for purposes of injection as liquid solutions or suspensions; however, solid forms suitable for solution or suspension in liquid prior to use may also be prepared.

Physiologically acceptable carriers are well known in the art. Exemplary liquid carriers for use in accordance with the present invention are sterile aqueous solutions which contain no materials other than the active ingredient and water, or may contain a buffer such as sodium phosphate at physiological pH value, physiological saline or both (i.e., phosphate-buffered saline). Suitable aqueous carriers may further comprise more than one buffer salt, as well as other salts (such as sodium and potassium chlorides) and/or other solutes.

The active ingredient may further be mixed in amounts suitable for use in the therapeutic methods described herein with one or more excipients which are pharmaceutically acceptable and compatible with the active ingredient. Suitable excipients include dextrose, glycerol, ethanol and the like, and combinations of one or more thereof with vegetable oils, propylene glycol, polyethylene glycol, benzyl alcohol and the like to provide a suitable injectable composition. In addition, if desired, the composition can contain wetting or emulsifying agents, isotonic agents, pH buffering agents, dissolution promoting agents, stabilizers, antiseptic agents and other typical auxiliary additives employed in the formulation of pharmaceutical preparations. In another variation, the active agents of the present invention may be incorporated into liposomal vesicles [see, e.g., U.S. Pat. Nos. 5,104,661; 5,013,556; and published PCT application WO 92/06192, the entire disclosures of which are hereby incorporated by reference]. Other suitable formulations for delivery of an active agent of general formula I would be immediately apparent to those working in the field. Typically, the compositions comprise at least about 0.1 weight percent to about 90 weight percent of therapeutic agent per weight of total therapeutic composition.

Determination of the appropriate amount of a compound of general formula I to administer to any given patient may routinely be determined empirically for the combination of patient and active agent. In general, an amount effective to achieve the desired effect is in the range of about 1 $\mu$g/kg to about 100 mg/kg of patient body weight, preferably about 1 to about 10 mg/kg.

In the course of developing the present invention, the activity of lidocaine was compared with another sodium channel blocker and with two lidocaine metabolites on tactile allodynia as measured in an experimental model for neuropathy in rats. Intravenous bupivacaine was inactive against allodynia; this substantiates previous similar observations with regard to the lack of effect of bupivacaine on centrally facilitated nociceptive processing [Biella G et al., Brain Res 603:201–206 (1992)]. Spinal sodium channel blockade likewise did not seem to be sufficient to reverse allodynia; when administered IT, lidocaine had no antiallodynic effect after termination of motor block [Chaplan S R et al., Anesthesiology 79:A910 (1993)]. Together, these observations immediately call into question the assumption that the effects of systemically administered lidocaine are attributable to the most salient pharmacological property of lidocaine, namely sodium channel blockade. 3-OH L did not cause motor block at an effective anti-allodynia dose.

Lidocaine had previously been shown to be effective against allodynia by the intravenous, but not the intrathecal/regional routes [Chaplan et al. (1993), supra]. Pursuant to the present invention, it is shown that 3-OH L lidocaine, but not MEGX, is an active metabolite of lidocaine with regard to allodynia suppression. 3-OH L was highly active when administered intravenously; allodynia suppression appeared at a lower total IV infused dose than previous results using the parent compound, arguing that IV 3-OH L is more potent with regard to this effect. Allodynia suppression also had far more rapid onset with 3-OH L, supporting the hypothesis that the metabolite is more specifically active than the parent compound. MEGX, by contrast, although an active antiarrhythmic agent [Narang P K et al., Clin Pharm Ther 24:654–662 (1978)], was completely devoid of anti-allodynia activity by the intravenous route at an exogenously administered dose designed to vastly exceed its appearance through biotransformation of an effective dose of systemically administered lidocaine.

3-OH L, and not MEGX, suppressed allodynia after IT administration. MEGX was administered in excess, at a dose sufficient to cause ample drug effect as witnessed by motor blockade. 3-OH L was administered at 10x lower concentration and yet effectively suppressed allodynia, with no evidence of motor effects.

Systemic lidocaine has been reported to have a long lasting effect by the IV route [Abram S E et al., Anesthesiology 80:383–391 (1994); Bach et al. (1990), supra; Chaplan et al. (1993), supra]. In the present observations, 3-OH L had a long lasting effect by the IT route, but not by the IV route. These observations are consistent with the hypotheses that 3-OH L or a closely related hepatic biotransformation product is the active agent in allodynia suppression, and the active site for this metabolite is in fact the spinal cord. This provides an explanation for the protracted activity of IT 3-OH L and not lidocaine after application to the cord, although the mechanism of effect remains unknown.

The efficacy of 3-OH L, but not MEGX, may explain the sporadic nature of long-lasting effects in humans. Predominance of one or the other metabolite is the result of the relative activity of differing hepatic enzymes in the P-450 system: 3-OH L is produced by the P450 PA(P45OIA2) enzyme, whereas MEGX is produced by the P45ONF (human) (P-450 PB-1(rat)(IIIA4) enzyme [Imaoka S et al., J Pharmacol Exp Ther 255:1385–1391 (1990)]. Pharmacogenetic or environmental, enzyme-inducing/suppressing factors may determine which patients produce meaningful levels of active metabolites vs. the predominant metabolite, MEGX.

Some species of rats predominantly produce 3-OH L. Thus, patients who inherently produce some 3-OH L, or who are subject to factors (such as illness, other medications) predisposing them to this hepatic P40 pathway, may exhibit long-lasting effects. Additionally, since humans do produce some 3-OH L, exposure to high doses of parent compound may force the production of pharmacologically active amounts of 3-OH L yielding the desired result (hence, the clinical popularity of subconvulsant doses of lidocaine given as isolated repeated infusions).

Systemic lidocaine had a sustained effect on tactile allodynia in SD rats but was not effective in this regard in DA rats. The reason for the lack of prolonged effect of lidocaine in DA rats is consistent with the documented lack of 3-hydroxylation in this strain, since a lower dose of the metabolite 3-OHL persistently reduced allodynia in both strains. Obvious reasons for the absence of this effect in human clinical use of lidocaine are that this unique property is not a property of the parent compound per se, and that humans are known to produce only very small quantities of 3-OHL.

The invention may be better understood with reference to the accompanying examples, which are intended for purposes of illustration only and should not be construed as in any sense limiting the scope of the invention as defined in the claims appended hereto.

EXAMPLES

Example 1

Male Harlan Sprague-Dawley rats were used (100–200 g). Rats were housed 2–3 to a cage with corn cob bedding and Purina rat chow and water ad libitum, in a standard facility with a 12 h/ 12 h day/night cycle. After surgical procedures involving chronic indwelling catheter insertion, animals were housed singly to prevent catheter damage.

To induce neuropathy, rats were anesthetized with halothane/oxygen, and the left L5/L6 spinal nerves were exposed via a dorsal midline incision and ligated tightly with 6-0 silk suture according to the reported method [Kim S H et al., Pain 50:355–363 (1992)]. Rats were allowed to recover 5–7 days before further testing or surgeries.

Intrathecal PE-10 catheters were implanted under halothane/oxygen anesthesia [Yaksh T L et al., Physiol Behav 17:1031–1036 (1976)]. The catheters were 9 cm in intrathecal length and terminated near the lumbar enlargement. The rostral 3 cm of catheter was tunneled under the skin to externalize between the ears. Rats with neurologic deficits were discarded.

For intravascular access, external jugular catheters were fashioned from PE-50 tubing and inserted into an external jugular vein under halothane/oxygen anesthesia. Arterial catheters were also fashioned from PE-50 with a small bouton 1 cm from the intravascular end for suture securing; they were inserted into a carotid artery, taking care to spare the surrounding nerves. All catheters were flushed with heparinized saline (10 U/ml) and tunneled subcutaneously to emerge at the posterior base of the neck, and capped when not in use.

Monoethylglycinexylidide (MEGX) was dissolved in physiologic saline; 3-hydroxylidocaine (3-OH L) was dissolved in DMSO for intravenous administration. For intrathecal administration, 3-OH L was dissolved in a vehicle consisting of 10% DMSO, 25% propylene glycol, 25% ethanol, and 40% physiologic saline, which was found to be less irritating than DMSO.

Intravenous drugs were delivered to awake, unrestrained rats by slow infusion using a syringe pump (Harvard apparatus 22). Intrathecal drugs were delivered to awake, briefly restrained rats in a volume of 10 $\mu$l, followed by 10 $\mu$l of vehicle flush, using a calibrated tubing extension with a 30-gauge adapter fitting the implanted intrathecal catheter, attached to a geared Hamilton 100 $\mu$l glass syringe. IT drug delivery was monitored by observing the advancement of a small air bubble down the tubing.

For bupivacaine assays, samples were obtained by withdrawing and discarding approximately 0.3 cc of blood from arterial cannulae, and then withdrawing samples of approximately 0.5 cc volume. These samples were centrifuged and the plasma supernatant was frozen at −20° C. until analysis.

Bupivacaine was extracted from the thawed samples by solid-phase extraction chromatography [Chen Y et al., Therapeut Drug Monitor 14:317–321 (1992)]. Sep-Pak C-18 (300 mg) cartridges were pre-conditioned with 4 ml of methanol and then 4 ml water. Internal standard (50 $\mu$l aqueous lidocaine HCl, equivalent to 2 ng/$\mu$l serum) was added to 200 $\mu$l serum and the mixture was vortexed for 30 seconds. The sample was applied to the cartridge and sequentially rinsed with 2 ml water, then 2 ml 25% methanol in water. Methanol (2×200 $\mu$l) was used to elute bupivacaine from the cartridges, and was removed by atmospheric evaporation at 45° C. Dried extracts were reconstituted in 100 $\mu$l anhydrous ethanol immediately prior to gas chromatographic (GC) analysis.

Bupivacaine was quantitated by capillary GC with nitrogen-phosphorus detection [Bjork M et al., Journal of Chromatography 533:229–234 (1990)]. A Hewlett-Packard 5890 II GC was equipped with a methyl-silicone gum (HP-1) capillary column (25M×0.2 mm×0.33 $\mu$M), programmed with injector and detector temperatures of 265° C. Split injections (1.5:1) were performed with a Hewlett Packard 7673A automatic sampler, and the chromatograms were recorded and analyzed with H-P Chemstation (MSDOS) software. The helium carrier gas flow rate was 0.9 ml/min (32 psi). Hydrogen and air flow-rates in the detector were 3 and 120 ml/min, respectively. The oven temperature was programmed at 240° C. for 1 minute, raised over 1 minute to a final temperature of 270° C., and held at 270° C. for 4 minutes. Total run time was 5 minutes; lidocaine and bupivacaine eluted at 2.4 and 4.0 minutes, respectively.

Rats were placed in a plastic cage with an open wire mesh bottom and allowed to accommodate for approximately fifteen minutes. A series of 8 von Frey filaments with logarithmically incremental stiffness (0.41, 0.70, 1.20, 2.00, 3.63, 5.50, 8.50, and 15.10 g) (Stoelting, Wood Dale, Ill.) was used to determine the 50% threshold for paw withdrawal to light mechanical stimuli (PWT). In brief, von Frey hairs were sequentially applied using an up-and-down paradigm to the left mid-plantar hindpaw with sufficient force to cause slight filament buckling. Positive responses were noted if the paw was sharply withdrawn. Previous observations had determined that normal or sham operated rats have PWT of $\geq$15 g. In cases where thresholds fell outside the range of detection, i.e., continuous positive or negative responses were observed to the limit of the range of stimuli, values of 15.00 g (normal) or 0.25 g (maximally neuropathic) were assigned respectively. Otherwise, PWT were calculated by noting the stimulus level at which the first change in behavior occurred, collecting four additional responses to the continued up-and-down oscillation of stimulus presentation around the response threshold, and interpolating the 50% response threshold. For some comparisons, raw thresholds were converted to percent of maximum possible effect (%MPE), designating pretreatment PWT (baselines) as 0% effect, and assigning a cutoff value of 100% effect to thresholds $\geq$15 g: therefore, %MPE values near 100 indicate normal mechanical thresholds (i.e., at or near 15 g), whereas values near 0 indicate allodynia. The following equation was used to compute %MPE:

$$\% MPE = \frac{\text{new threshold (g)} - \text{baseline threshold (g)}}{15 \text{ grams} - \text{baseline threshold}} \times 100$$

Plasma drug levels and PWT were correlated using linear regression. Serially measured PWT and %MPE were compared using repeated measures ANOVA.

Intravenous infusion of bupivacaine had no effect on allodynia (15 samples from 4 rats, P=0.11, linear regression), up to plasma concentrations which caused evident toxicity as manifested by ataxia and lethargy. Higher doses resulted in seizure (mean plasma level, 7.4±0.7), N=4). FIG. 1 displays the lack of correlation between plasma bupivacaine levels and % MPE on PWT.

Figure 2:
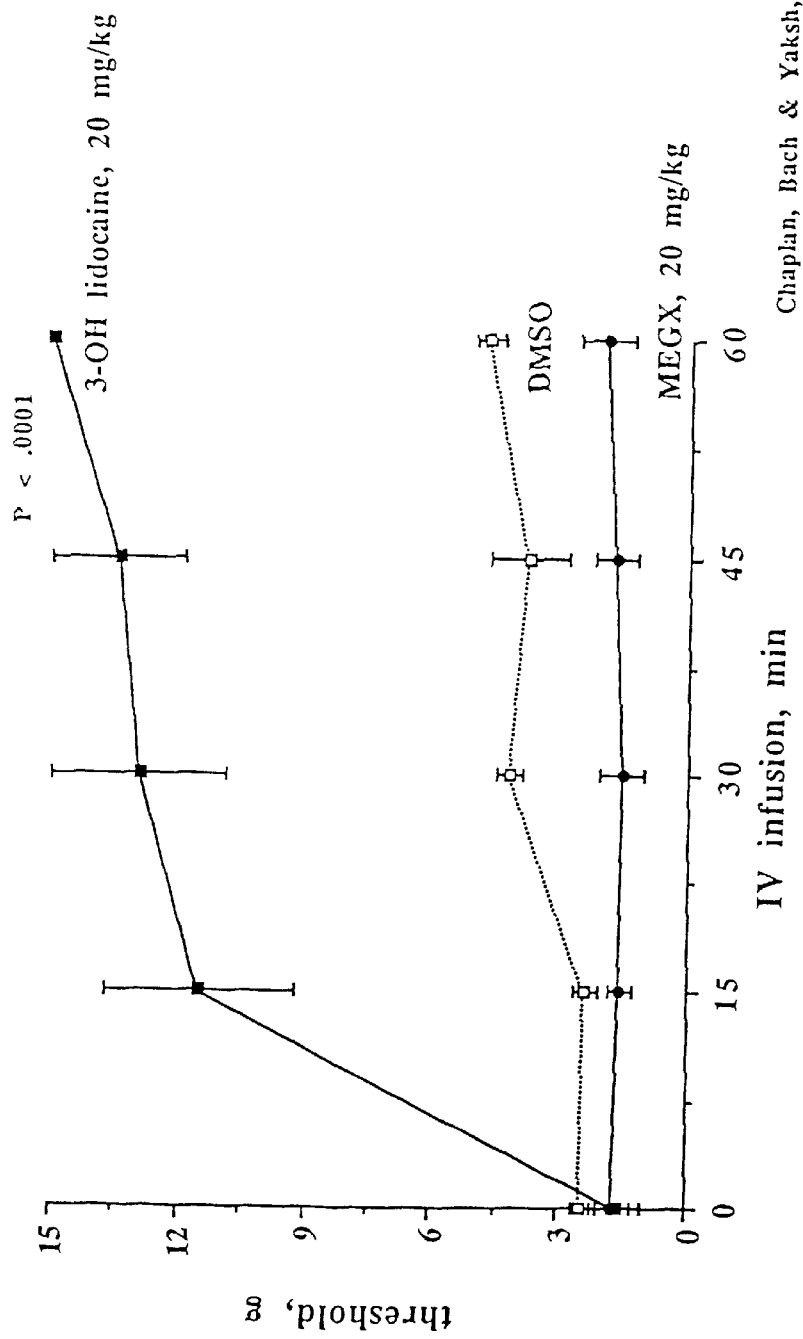
FIG. 2 illustrates the effect of constant-rate infusion of lidocaine metabolites 3-OH L (20 mg/kg total), MEGX (20 mg/kg, total) and the vehicle for 3-OH, DMSO, on paw withdrawal thresholds (allodynia) (N=4 rats per group)
Figure 3:
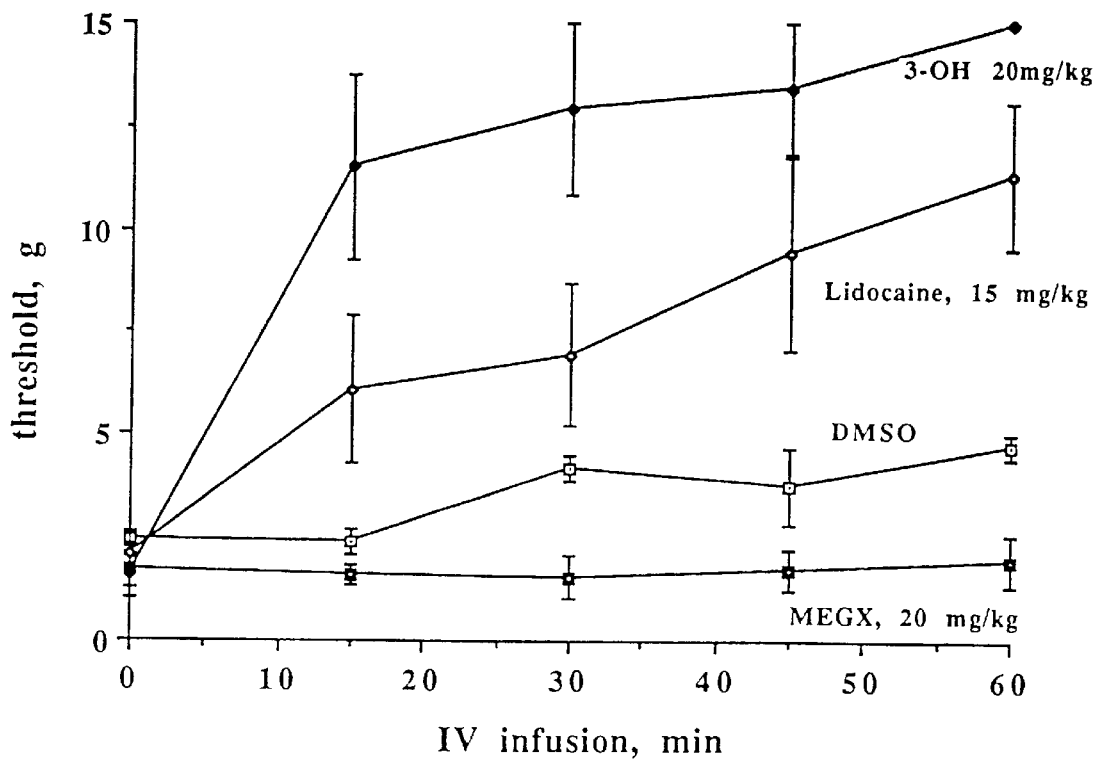
FIG. 3 is data from FIG. 2 with superimposed data for the IV administration of lidocaine, 15 mg/kg (N=6 rats) showing effects on rat paw thresholds (allodynia)

By IV delivery 3-OH L (in DMSO) was both potent and effective at suppressing allodynia (N=4). Maximum effect on PWT was complete normalization (15±0 g after infusion, compared to 1.57±0.5 g at baseline, P=<0.0001, repeated measures ANOVA). MEGX had no effect whatsoever at a dose of 20 mg/kg, infused over 60 minutes (baseline, 1.7±0.6 g; post infusion 1.96±0.4 g). FIG. 2 shows the effect on PWT at time points after infusion of the respective metabolites/vehicles. For the purpose of comparison with lidocaine, FIG. 3 shows the data from FIG. 2 with the additional superimposition of a data set for the intravenous infusion of a nearly comparable dose of lidocaine, 15 mg/kg.

Figure 4:
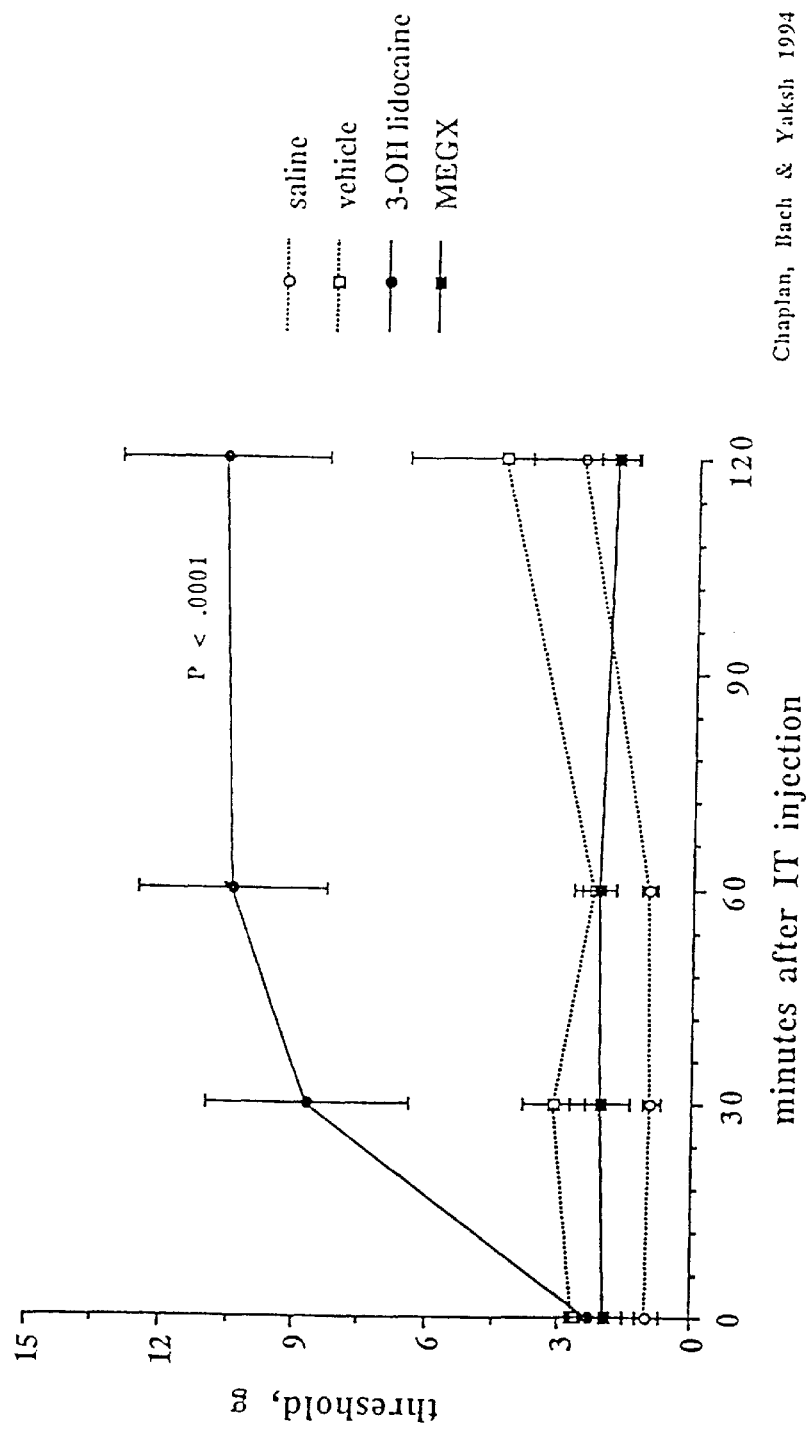
FIG. 4 depicts the effect of the intrathecal administration of limiting doses of MEGX (500 μg, limited by motor effect), 3-OH L (intrathecal injection, 58 μg, limited by solubility) and their respective vehicles on allodynia, measured as paw withdrawal thresholds (N=6 rats per group)

The IT delivery of lidocaine, 500 $\mu$g, resulted in the acute onset of hindquarter flaccidity of approximately 10 minutes duration, during which time it was not possible to measure PWT. After recovery of motor function, allodynia thresholds remained indistinguishable from pre-drug baseline (i.e., no effect on allodynia was seen). The IT administration of 500 μg MEGX resulted in transient motor dysfunction (5–10 minutes), manifested as hindquarter weakness; after this weakness resolved, rat behavior appeared normal. MEGX showed no effect on PWT at this limiting dose, similar to observations made with lidocaine. In contrast, no motor dysfunction was seen after 3-OH L injection at the highest dose soluble in the vehicle, 58 μg. 3-OH L lidocaine was significantly effective at suppressing allodynia: baseline thresholds were 2.3±0.39 g, compared to 10.66±2.3 g at 60 minutes after treatment (P<0.0001). FIG. 4 shows the effect on PWT of IT administration of MEGX, 3-OH L, and the combination vehicle for 3-OH L, at time points after acute treatment.

Figure 5:
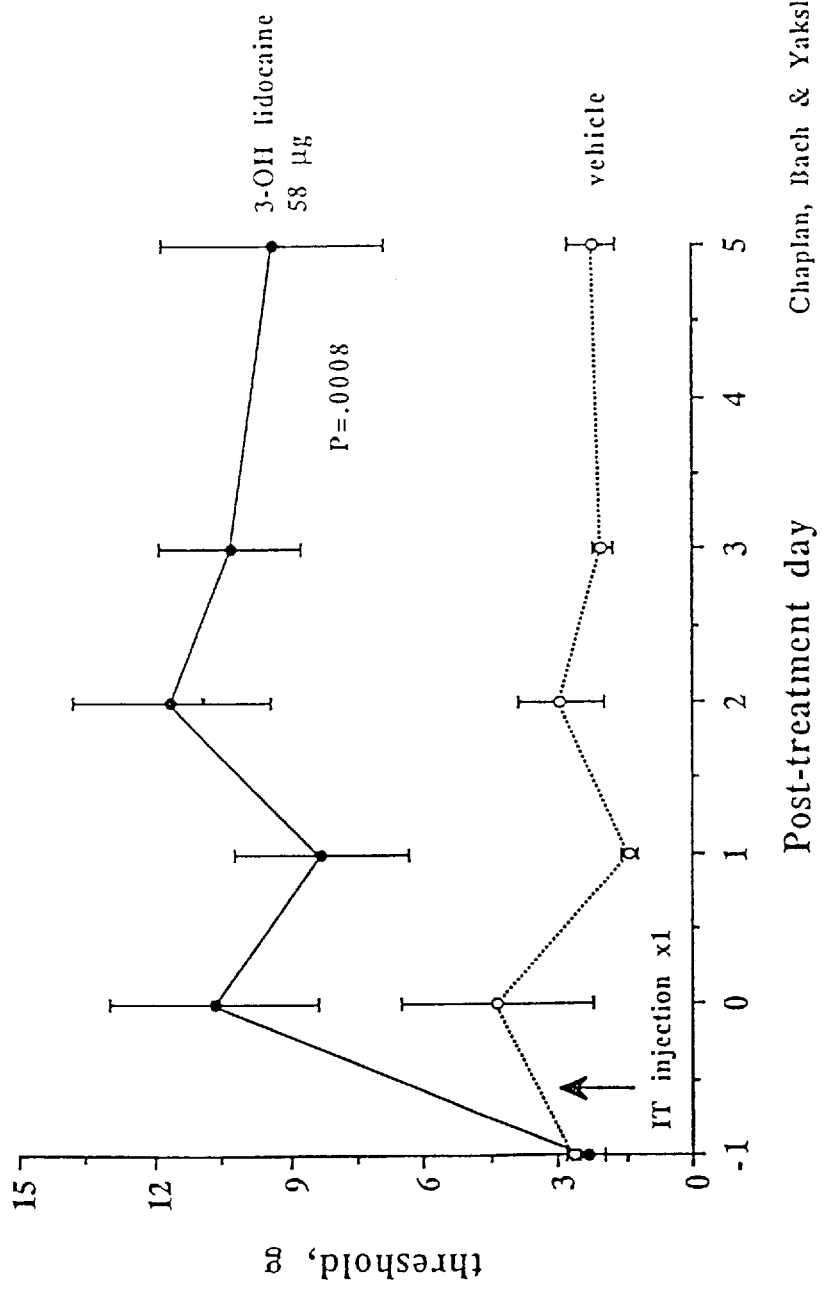
FIG. 5 shows the persistence of the allodynia suppressing effect of IT 3-OH L, 58 μg, compared to vehicle over a 5 day observation period (N=6 rats per group)

Long term effects of IT 3-OH L were determined. The allodynia suppression by 3-OH L, 58 μg single dose (administered in the combination vehicle described above) persisted for the 5 day follow-up period, without signs of motor or behavioral toxicity. Thresholds at 5 days post treatment (N=6) were 9.3±2.5, significantly greater than baseline (2.7±0.2) and concurrent vehicle controls (N=6) (2.2±0.5) (P=0.0008, repeated measures ANOVA). FIG. 5 shows the PWT during the 5 day follow-up period for 3-OH L versus vehicle.

Example 2

12 SD rats (140–170 g) and 12 DA rats (120–145 g) underwent tight ligation of the left L5 and L6 spinal nerves as described above under general anesthesia consisting of barbiturate/benzodiazepine i.p. Rats were allowed 7 days recovery. Postoperatively, all displayed mechanical allodynia, defined as left hindpaw withdrawal thresholds of <4 g as quantified with Von Frey hairs. 2% Lidocaine HCl (Astra) was commercially obtained and diluted in physiologic saline; 3-OHL was diluted in DMSO.

Six rats of each strain received a single dose of lidocaine 60 mg/kg i.p., and the other 6 an equivalent volume of saline. Mechanical thresholds were tested repeatedly and compared for 20 days following drug dosing.

Six weeks after lidocaine administration, all thresholds had returned to baseline. We studied 10 DA rats and 12 SD rats: half of each group received 3-OHL 15 mg/kg i.p., and the remainder received an equivalent volume of DMSO alone. Thresholds were followed for 7 days.

Figure 6:
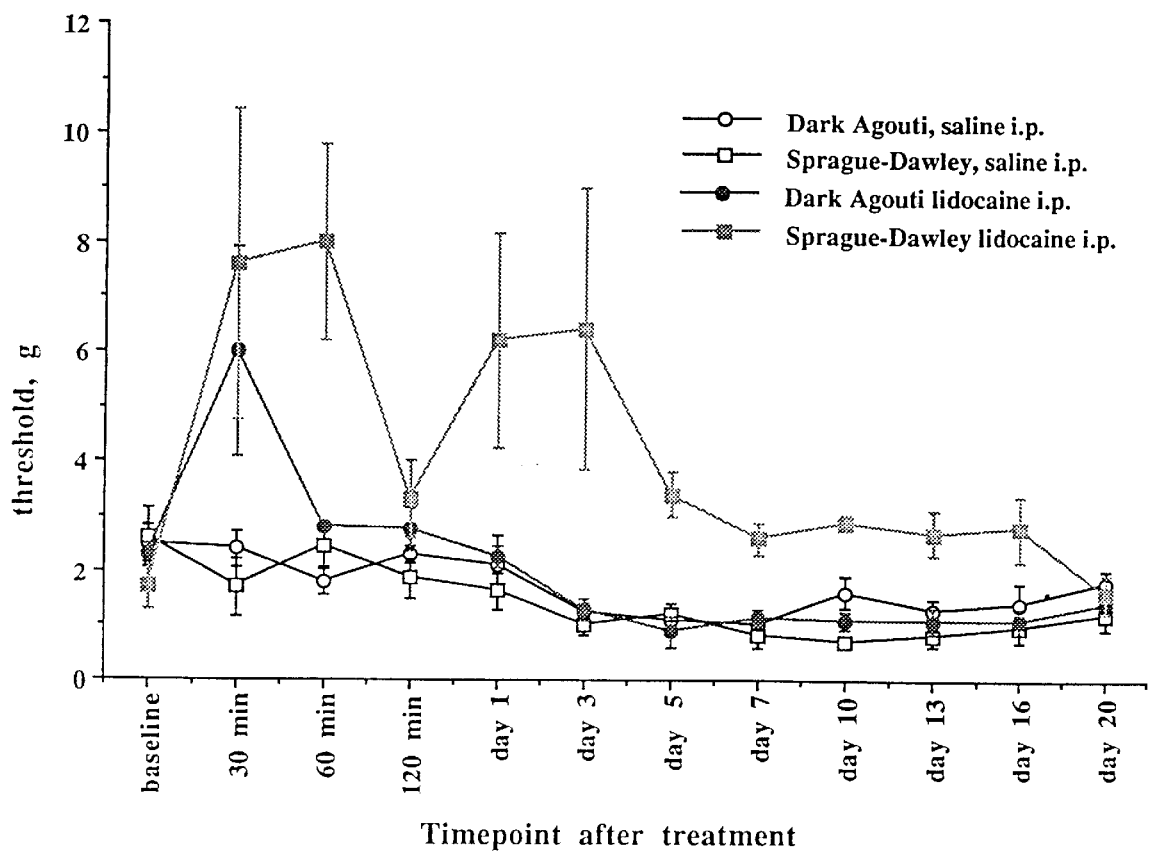
FIG. 6 shows the results in SD rats (N=12) and DA rats (N=12) given either a single dose of lidocaine 60 mg/kg, i.p. (N=6, each strain) or saline (N=6, each strain)

Lidocaine alleviated tactile allodynia for more than 16 days in SD rats. There was a transient effect at 30 minutes, but no sustained effect whatsoever, in DA rats. The difference for strain was significant (P<0.002). After surgical neuropathy creation and baseline allodynia measurements, SD rats (N=12) and DA rats (N=12) were given either a single dose of lidocaine 60 mg/kg, i.p. (N=6, each strain) or saline (N=6, each strain). Paw withdrawal thresholds (g) were measured at the timepoints depicted until 20 days after drug administration. There was a significant inter-strain difference with SD rats showing persistent effects of lidocaine against allodynia (P<0.002, ANOVA) (FIG. 6).

Figure 7A:
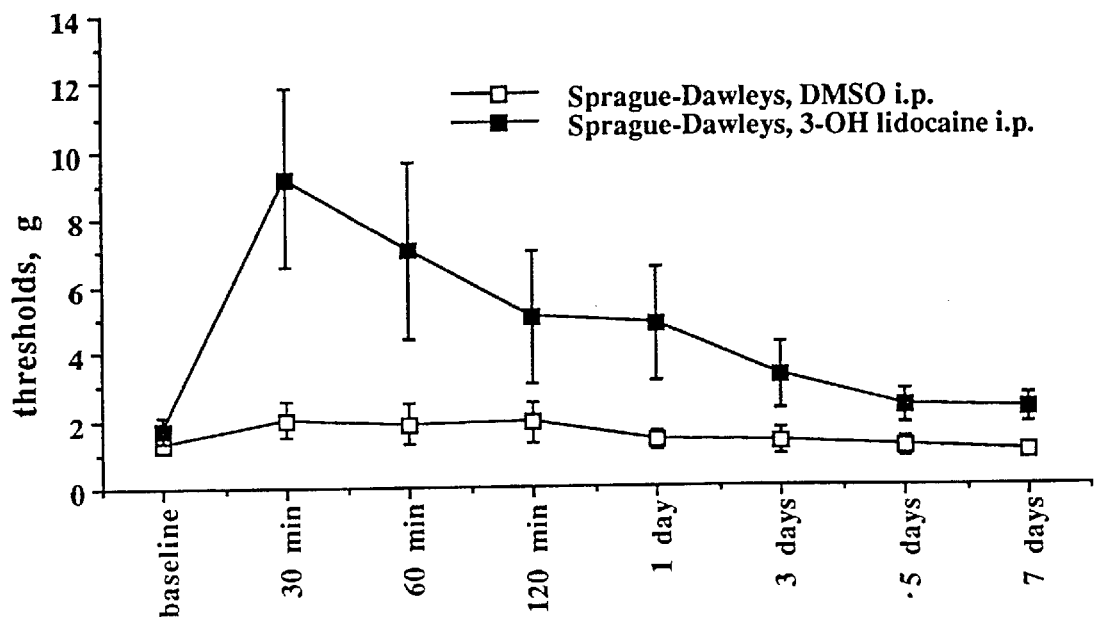
FIG. 7 shows the results in SD rats (N=6) and DA rats (N=5) given i.p. 3-OHL 15 mg/kg or DMSO vehicle alone.
Figure 7B:
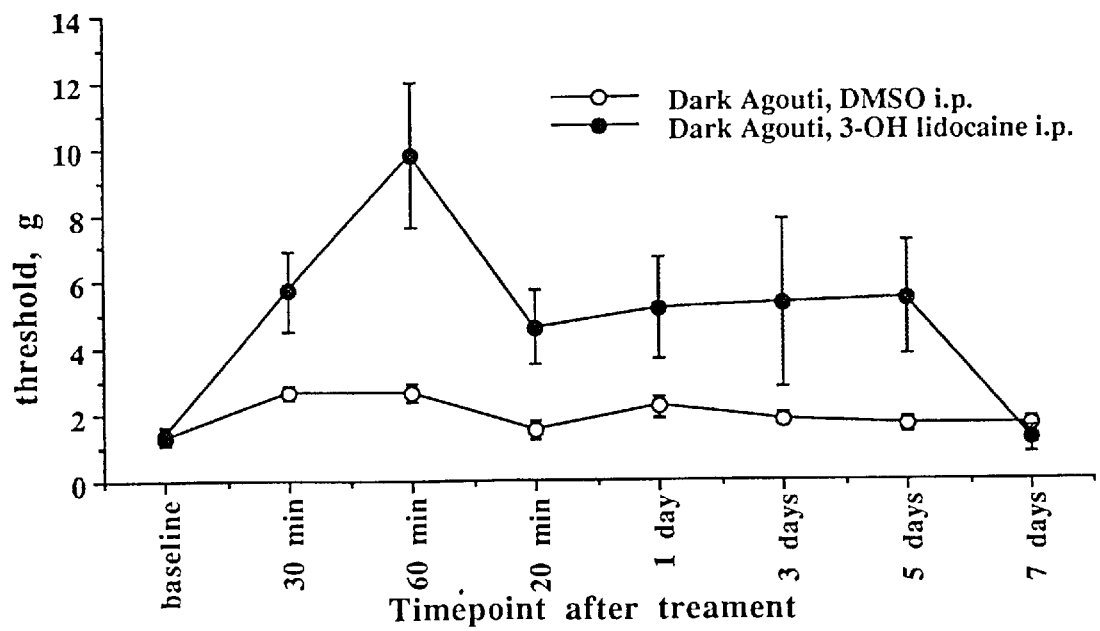

Whereas there was no sustained effect of lidocaine in DA rats, 3-OHL had a significant effect on allodynia for up to 7 days in both SD and DA rats. SD rats (N=6) and DA rats (N=5) were given i.p. 3-OHL 15 mg/kg; equal numbers of each strain were given DMSO vehicle alone. Paw withdrawal thresholds (g) were followed for 7 days. Both strains showed significant (P<0.05 SD's; P<0.002 DA's) persistent suppression of allodynia (ANOVA, repeated measures). The magnitude of the effect of 15 mg/kg of 3-OHL was similar to the effect in SD rats of 60 mg/kg lidocaine (FIG. 7) with an apparently shorter duration. No motor or other evident toxic effects were seen from either drug.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and any specific terms employed herein are intended in a descriptive sense and not for purposes of limitation.

What is claimed is:

1. A method for alleviating neuropathic pain in a mammalian patient, comprising administering to the patient an amount effective to alleviate neuropathic pain of a physiologically acceptable salt of at least one compound of general formula I

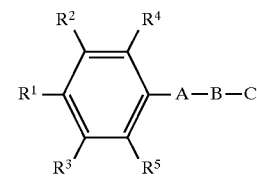

wherein each of $R^1$, $R^2$ and $R^3$ is independently selected from the group consisting of hydrogen, hydroxyl, acyl, alkoxyl, alkyl, aryl, alkylaryl, arylalkyl, hydroxyalkyl, hydroxyaryl, alkoxyalkyl, alkoxyaryl and $NR^8R^9$, in which each of $R^8$ and $R^9$ is independently selected from the group consisting of hydrogen, alkyl, aryl, acyl, alkylaryl, arylalkyl, hydroxyalkyl, hydroxyaryl, alkoxyalkyl and alkoxyaryl, with the proviso that at least one of $R^1$, $R^2$ and $R^3$ is hydroxyl;

each of $R^4$ and $R^5$ is independently selected from the group consisting of hydrogen, halogen and lower alkyl;

A is —C(=O)O— or $NR^{10}C(=O)$—, in which $R^{10}$ is selected from the group consisting of hydrogen, alkyl, aryl, alkylaryl, arylalkyl, hydroxyalkyl, hydroxyaryl, alkoxyalkyl and alkoxyaryl;

B is —$(CR^{11}R^{12})_n$—, in which each of $R^{11}$ and $R^{12}$ is independently selected from the group consisting of hydrogen, halogen, hydroxyl, alkoxyl, alkyl, aryl, acyl, alkylaryl, arylalkyl, hydroxyalkyl, hydroxyaryl, alkoxyalkyl and alkoxyaryl, and n is an integer from 1 to 5; and C is $NR^6R^7$, in which each of $R^6$ and $R^7$ is independently selected from the group consisting of hydrogen, alkyl, aryl, acyl, alkylaryl, arylalkyl, hydroxyalkyl, hydroxyaryl, alkoxyalkyl and alkoxyaryl, or $R^6$ and $R^7$ together form a heterocycle or substituted heterocycle selected from the group consisting of piperidyl, N-alkylpiperidyl, piperazinyl, N'-alkylpiperazinyl, morpholinyl and N-alkylmorpholinyl, in a suitable carrier or excipient.

2. A method according to claim 1, wherein the at least one compound of general formula I is administered at a rate of about 1 μg/kg to about 100 mg/kg of patient body weight.

3. A method according to claim 2, wherein the at least one compound of general formula I is administered at a rate of about 1 to about 10 mg/kg of patient body weight.

4. A method according to claim 1, wherein the at least one compound of general formula I is solubilized by conjugation.

5. A method according to claim 4, wherein the at least one compound of general formula I is glucuronidated.

6. A method according to claim 1, wherein the at least one compound of general formula I is administered orally.

7. A method according to claim 1, wherein the at least one compound of general formula I is administered intravenously.

8. A method according to claim 1, wherein the at least one compound of general formula I is administered intrathecally.

9. A method according to claim 1, for treatment of allodynia.

10. A composition for alleviating neuropathic pain in a mammalian patient, consisting essentially of physiologically active material and suitable carrier or excipient material, said physiologically active material comprising an amount effective to alleviate neuropatic pain of a physiologically-acceptable salt of at least one compound of general formula I

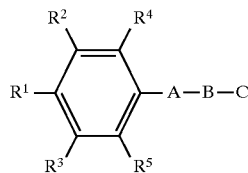

wherein each of $R^1$, $R^2$ and $R^3$ is independently selected from the group consisting of hydrogen, hydroxyl, acyl, alkoxyl, alkyl, aryl, alkylaryl, arylalkyl, hydroxyalkyl, hydroxyaryl, alkoxyalkyl, alkoxyaryl and $NR^8R^9$, in which each of $R^8$ and $R^9$ is independently selected from the group consisting of hydrogen, alkyl, aryl, acyl, alkylaryl, arylalkyl, hydroxyalkyl, hydroxyaryl, alkoxyalkyl and alkoxyaryl, with the proviso that at least one of $R^1$, $R^2$ and $R^3$ is hydroxyl;

each of $R^4$ and $R^5$ is independently selected from the group consisting of hydrogen, halogen and lower alkyl, with the proviso that only one of $R^4$ and $R^5$ is hydogen;

A is —C(=O)O— or $NR^{10}C(=O)$—, in which $R^{10}$ is selected from the group consisting of hydrogen, alkyl, aryl, alkylaryl, arylalkyl, hydroxyalkyl, hydroxyaryl, alkoxyalkyl and alkoxyaryl;

B is —$(CR^{11}R^{12})_n$—, in which each of $R^{11}$ and $R^{12}$ is independently selected from the group consisting of hydrogen, halogen, hydroxyl, alkoxyl, alkyl, aryl, acyl, alkylaryl, arylalkyl, hydroxyalkyl, hydroxyaryl, alkoxyalkyl and alkoxyaryl, and n is an integer from 1 to 5; and C is $NR^6R^7$, in which each of $R^6$ and $R^7$ is independently selected from the group consisting of hydrogen, alkyl, aryl, acyl, alkylaryl, arylalkyl, hydroxyalkyl, hydroxyaryl, alkoxyalkyl and alkoxyaryl, or $R^6$ and $R^7$ together form a heterocycle or substituted heterocycle selected from the group consisting of piperidyl, N-alkylpiperidyl, piperazinyl, N'-alkylpiperazinyl, morpholinyl and N-alkylmorpholinyl.

11. A composition according to claim 10, comprising a unit dosage form wherein the at least one compound of general formula I is provided at a rate of about 1 μg/kg to about 100 mg/kg of patient body weight.

12. A composition according to claim 11, wherein the at least one compound of general formula I is provided at a rate of about 1 to about 10 mg/kg of patient body weight.

13. A composition according to claim 10, wherein the at least one compound of general formula I is solubilized by conjugation.

14. A composition according to claim 13, wherein the at least one compound of general formula I is glucuronidated.

15. A composition according to claim 10, formulated for administration orally.

16. A composition according to claim 10, formulated for administration intravenously.

17. A composition according to claim 10, formulated for administration intrathecally.

18. A method according to claim 1 wherein $R^1$ is H, $R^2$ is OH, $R^3$ is H, $R^4$ is $CH_3$, $R^5$ is $CH_3$, A is —NHC(=O)—, B is —$(CHR^{12})$— in which $R^{12}$ is selected from the group consisting of hydrogen, methyl and ethyl, and C is —$NR^6R^7$ in which $R^6$ is selected from the group consisting of hydrogen and an alkyl group and $R^7$ is an alkyl group, said alkyl group in each case being selected from —$C_2H_5$ and —$C_3H_7$.

19. A method for alleviating pain in a mammalian patient, comprising administering to the patient an amount effective to alleviate pain of a physiological-acceptable salt of 3-hydroxylidocaine.

20. A composition according to claim 10 wherein $R^1$ is H, $R^2$ is OH, $R^3$ is H, $R^4$ is $CH_3$, $R^5$ is $CH_3$, A is —NHC(=O)—, B is —$(CHR^{12})$— in which $R^{12}$ is selected from the group consisting of hydrogen, methyl and ethyl, and C is —$NR^6R^7$ in which $R^6$ is selected from the group consisting of hydrogen and an alkyl group and $R^7$ is an alkyl group, said alkyl group in each case being selected from —$C_2H_5$ and —$C_3H_7$.

21. A composition for alleviating pain in a mammalian patient, consisting essentially of physiologically active material and a suitable carrier or excipient, said physiologically active material comprising an amount effective to alleviate pain of a physiological-acceptable salt of 3-hydroxylidocaine.

22. A composition for alleviating neuropathic pain in a mammalian patient, consisting essentially of physiologically active material and suitable carrier or excipient material, said physiologically active material comprising an amount effective to alleviate neuropatic pain of a physiologically-acceptable salt of at least one compound of general formula I

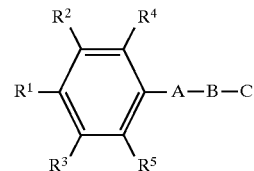

wherein each of $R^1$, $R^2$ and $R^3$ is independently selected from the group consisting of hydrogen, hydroxyl, acyl, alkoxyl, alkyl, aryl, alkylaryl, arylalkyl, hydroxyalkyl, hydroxyaryl, alkoxyalkyl, alkoxyaryl and $NR^8R^9$, in which each of $R^8$ and $R^9$ is independently selected from the group consisting of hydrogen, alkyl, aryl, acyl, alkylaryl, arylalkyl, hydroxyalkyl, hydroxyaryl, alkoxyalkyl and alkoxyaryl, with the proviso that at least one of $R^1$, $R^2$ and $R^3$ is hydroxyl;

each of $R^4$ and $R^5$ is independently selected from the group consisting of hydrogen, halogen and lower alkyl;

A is $NR^{10}C(=O)$—, in which $R^{10}$ is selected from the group consisting of hydrogen, alkyl, aryl, alkylaryl, arylalkyl, hydroxyalkyl, hydroxyaryl, alkoxyalkyl and alkoxyaryl;

B is —$(CR^{11}R^{12})_n$—, in which each of $R^{11}$ and $R^{12}$ is independently selected from the group consisting of hydrogen, halogen, hydroxyl, alkoxyl, alkyl, aryl, acyl, alkylaryl, arylalkyl, hydroxyalkyl, hydroxyaryl, alkoxyalkyl and alkoxyaryl, and n is an integer from 1 to 5; and C is $NR^6R^7$, in which each of $R^6$ and $R^7$ is independently selected from the group consisting of hydrogen, alkyl, aryl, acyl, alkylaryl, arylalkyl, hydroxyalkyl, hydroxyaryl, alkoxyalkyl and alkoxyaryl, or $R^6$ and $R^7$ together form a heterocycle or substituted heterocycle selected from the group consisting of piperidyl, N-alkylpiperidyl, piperazinyl, N'-alkylpiperazinyl, morpholinyl and N-alkylmorpholinyl.

* * * * *

UNITED STATES PATENT AND TRADEMARK OFFICE
CERTIFICATE OF CORRECTION

PATENT NO. : 5,849,737
DATED : December 15, 1998
INVENTOR(S) : Sandra Reading Chaplan, Flemming Winther Bach, Tonly Lee Yaksh It is certified that error appears in the above-identified patent and that said Letters Patent is hereby corrected as shown below:

On the title page, item

[56] References Cited U.S. PATENT DOCUMENTS insert the following:

3,689,555 9/1972 Schut et al.
    4,532,248 7/1985 Molnar et al.
    5,496,854 3/1996 Keinan

OTHER PUBLICATIONS

Abu-Shady, H. et al., "Synthesis of some 4-aminophenol derivatives of expected pharmacodynamic activity", *Chemical Abstracts*, Abstract No. 477795 (1976) [Egypt. J. Pharm. Sci. 16(3):289-96(1976)]

Sudaka et al (FR 2068405, *Chemical Abstracts* AN 1972:149236

Column 3, line 2, change "in vivo" to --*in vivo*--

Signed and Sealed this

Twenty-eighth Day of September, 1999

*Attest:*

Q. TODD DICKINSON

*Attesting Officer*      *Acting Commissioner of Patents and Trademarks*